US007071162B1

(12) United States Patent
Narayanan et al.

(10) Patent No.: US 7,071,162 B1
(45) Date of Patent: Jul. 4, 2006

(54) COMBINED USE OF CEMENTUM ATTACHMENT PROTEIN AND CYCLOSPORIN A FOR IMPROVED ATTACHMENT OF DENTAL AND ORTHOPEDIC IMPLANTS

(76) Inventors: A. Sampath Narayanan, University of Washington, Room C-525, Health Sciences Bldg., Box 357470, Seattle, WA (US) 98195; Sandu Pitaru, Ben Elizer Street 46, Ramat Gan, 52290, Tel Aviv (IL); Roy C. Page, 8631 Inverness Dr., N.E., Seattle, WA (US) 98115; Anthony C. Allison, 2153 Hastings Dr., Belmont, CA (US) 94002

( * ) Notice: Subject to any disclaimer, the term of this patent is extended or adjusted under 35 U.S.C. 154(b) by 532 days.

(21) Appl. No.: 10/410,762

(22) Filed: Apr. 9, 2003

Related U.S. Application Data

(63) Continuation-in-part of application No. 09/367,168, filed on Nov. 15, 1999, now abandoned, which is a continuation-in-part of application No. PCT/US98/26396, filed on Dec. 11, 1998.

(60) Provisional application No. 60/069,638, filed on Dec. 15, 1997.

(51) Int. Cl.
*A61K 38/02* (2006.01)
*A61K 38/12* (2006.01)
*A61K 38/16* (2006.01)

(52) U.S. Cl. .............................. 514/12; 514/9; 514/11; 530/350; 530/317

(58) Field of Classification Search .................. 514/2, 514/12, 9, 11; 530/377, 350
See application file for complete search history.

(56) References Cited

U.S. PATENT DOCUMENTS

| | | | |
|---|---|---|---|
| 4,659,561 A | 4/1987 | Fives-Taylor et al. |
| 4,944,754 A | 7/1990 | Linkow et al. |
| 5,002,583 A | 3/1991 | Pitaru et al. |
| 5,124,316 A | 6/1992 | Antoniades et al. |
| 5,418,221 A | 5/1995 | Hammarstrom et al. |

OTHER PUBLICATIONS

Allison, A., "Mechanisms of action of mycophenolate mofetil in preventing chronic rejection", article, Transplantation Proceedings, V 34, pp 2863–6, 2002.
Ayanoglou, C., et al., "New cementum formation induced by cyclosporin A: a histological, ultrastructural and histomorphometric study in the rat", article, J Periodont Res, V32, pp 543–56, 1997.
Balshi, T., DDS, "An analysis and management of fractured implants: a clinical report", article, Int J Oral Maxilofac Implants, V 11, pp 660–6, 1996.

Buser, D., et al., "Soft tissue reactions to non–submerged unloaded titanium implants in beagle dogs", article, J Periodontal, v 63, pp 226–36, 1992.
Buser, D., et al., "Titanium implants with a ture periodontal ligament: an alternative to osseontegrated implants?", article, Int J Oral Masillofac Implants, V 5, pp 113–6, 1990.
Caffesse, R., DDS et al., "Regeneration of soft and hard tissue periodontal defects", article Am J Dentistry, V 15, N 5, pp 339–45, Oct. 2002.
Consensus Report, Implant Therapy I, Section 9, Ann Periodontal, V 1, N 1, pp 792–5, Nov. 1996.
Consensus Report, Implant Therapy II, Section 10, Ann Periodontal, V 1, N 1, Nov. 1996.
Hammarstrom, L., et al., "Periodontal regeneration in a buccal dihiscence model in monkeys after application of enamel matrix proteins", article, J Clin Periodonal, V 24, pp 669–677, 1997.
Ikezawa, K., et al., "Characterization of cementum derived growth factor as an insulin–like growth factor–I like molecule", article, Connective Tissue Research, V 364, N 4, pp 309–19, 1997.
Isobe, M., et al., "Bone morphogenetic protein encapsulated with a biodegradable and biocompatible polymer", article, J Biomedical Materials Research, V 32, pp 433–8, 1996.
Meier–Kriesche, H., et al., "Long–term use of mycophenolate mofetil is associated with a reduction in the incidence and risk of late rejection", article, Am J Transplantation, V 3, pp 68–73, 2003.
Metzger, Z., et al., "Differential chemotactic effect of cementum attachment protein on periodontal cells", article, J Periodont Res, V 33, pp 126–9, 1998.
Nagaishi, M., "Effect of various implant materials on cementogenesis", abstract, J Japanese Assoc of Periodontolgy, V 31, N 2, pp 551–72, Jun. 1989.
Narayanan, A., et al., "Biochemistry of periodontal connective tissues and their regeneration: a current perspective", article, Connective Tissue Research, V 343, N 3, pp 191, 201, 1996.

(Continued)

*Primary Examiner*—Michael Borin
(74) *Attorney, Agent, or Firm*—The Luther Law Firm; Barbara J. Luther

(57) ABSTRACT

A method is described for inducing the formation of cementum and a periodontal ligament between a dental implant and bone by administering cementum attachment protein (CAP) together with a calcineurin inhibitor such as cyclosporin A (CSA). Also contemplated is an implant kit comprising a titanium or other biologically inert dental or orthopedic implant and a coating of CAP and a calcineurin inhibitor such as CSA. Furthermore, application of CAP and CSA to dental root surfaces can be used to induce the regeneration of a periodontal ligament during treatment for periodontal disease. A similar method for reattaching a fibrous structure, such as a tendon, ligament or joint capsule, to bone is described.

10 Claims, 3 Drawing Sheets

OTHER PUBLICATIONS

Narayanan, S., et al., "Purification and characterization of a novel growth factor from cementum", article, J Periodont Res, V 28, pp 563–5, 1993.

Needleman, J., et al., "A systematic review of guided tissue regeneration for periodontal infrabony defects", article, J Periodont Res, V 37, pp 380–8, 2002.

Pitaru, S., et al., "Binding of a cementum attachment protein to extracellular matrix components and to dental surfaces", article, J Periodont Res V 27, pp 640–646, 1992.

Pitaru, S., et al., "Molecular and cellular interactions of a cementum attachment protein with periodontal cells and cementum matrix components", article, J Periodont Res, V 28, pp 560–2, 1993.

Pitaru, S., et al., "Specific cementum attachment protein enhances selectively the attachment and migration of periodontal cells to root surfaces", J Periodont Res, V 30, pp 360–8, 1995.

Schou, S., et al., "Ligature–induced marginal inflammation around osseointegrated implants and ankylosed teeth: stereologic and histologic and observations in cynomolgus monkeys (Macaca fascicularis)"; article, J Periodontal, V 64, pp 529–37, 1993.

Tooms, R., et al., "Arthroplasty Introduction and overview", Chapter 14, Campbell's Operative Orthopaedics, 8th edition, ed by A. H. Crenshaw, MD, V 1, pp 371–87.

Wilbert, H., et al., "Reaction of bone to methacrylate after hip arthroplasty", article, J Bone Joint Surg, pp 1368–82.

Wu, D., et al., "Characterization of a collagenous cementum–derived attachment protein", article, J Bone Mineral Res, V 11, N 5, pp 686–92, Nov. 5, 1996.

Honemura, K., et al., "Mitogenic signaling mechanisms of human cementum–derived growth factor", article, J Bio Chem, V 268, N 35, pp 26120–6, Dec. 15, 1993.

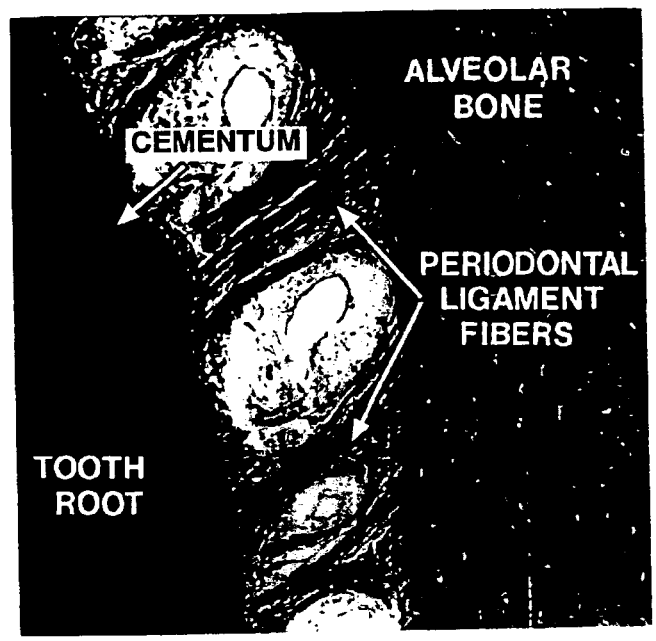
FIG._1
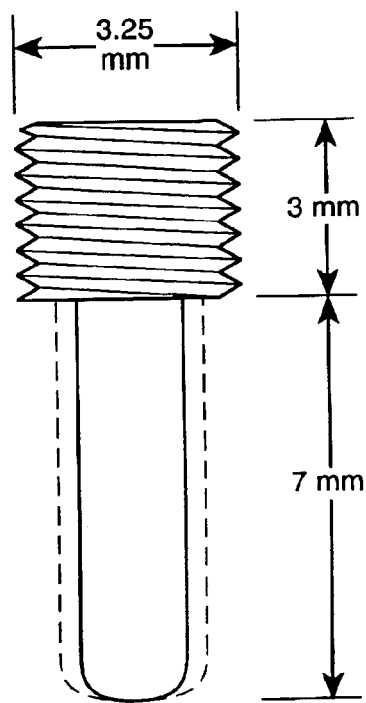
FIG._2

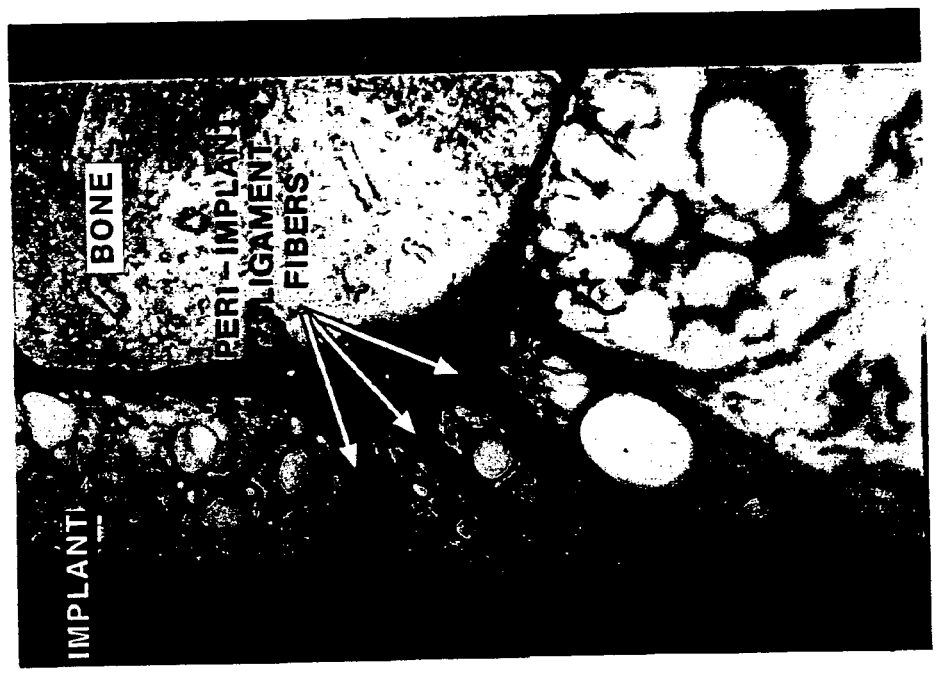
FIG._3B
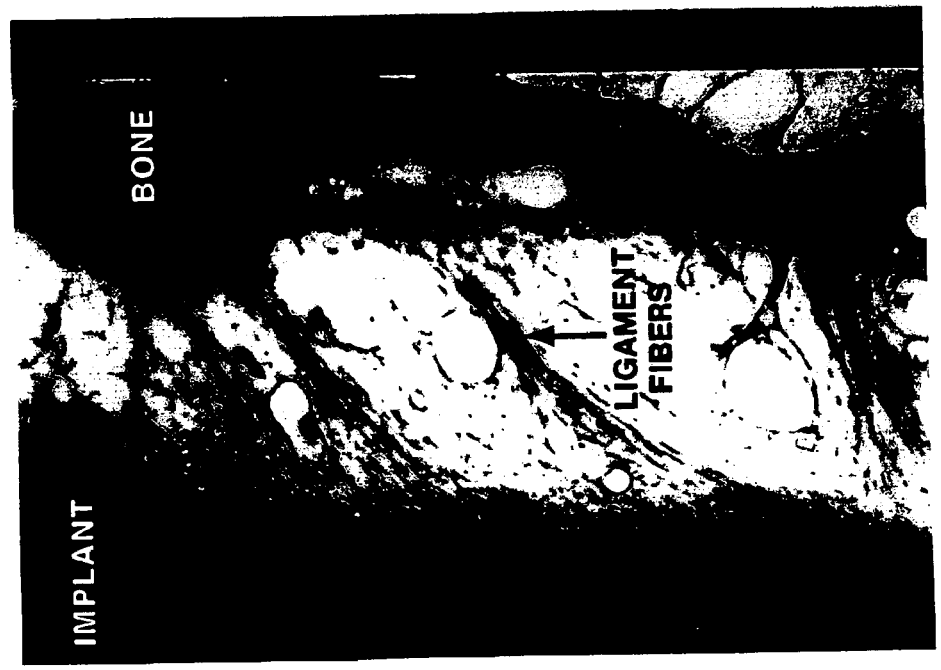
FIG._3A

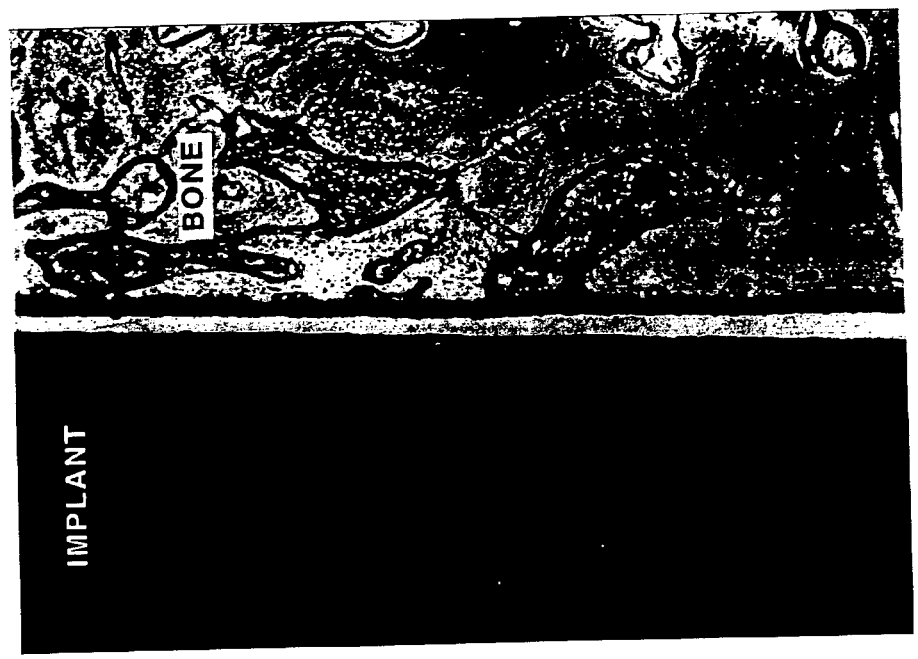
FIG._3D
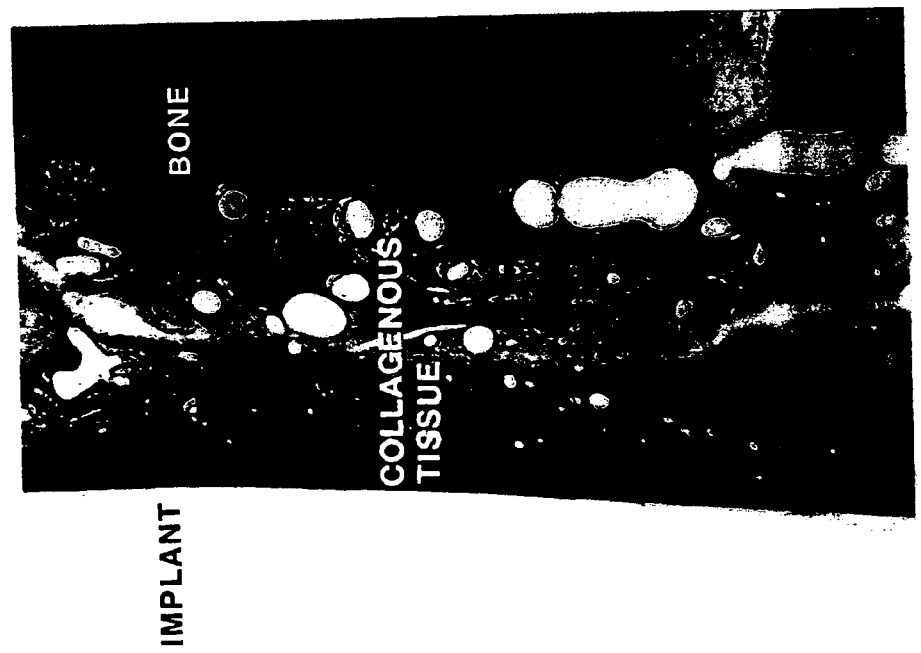
FIG._3C

US 7,071,162 B1

COMBINED USE OF CEMENTUM ATTACHMENT PROTEIN AND CYCLOSPORIN A FOR IMPROVED ATTACHMENT OF DENTAL AND ORTHOPEDIC IMPLANTS

CROSS-REFERENCE TO RELATED APPLICATIONS

This application is a continuation-in-part of U.S. application Ser. No. 09/367,168, filed Nov. 15, 1999, which is a continuation-in-part of International Application No. PCT/US98/26396 filed Dec. 11, 1998, which application claims the benefit of U.S. Provisional Application No. 60/069,638 filed Dec. 15, 1997.

STATEMENT REGARDING FEDERALLY SPONSORED RESEARCH

This invention was partially made with Government support under Grant Nos. DE 10491 and DE 08229 awarded by the National Institute for Dental Research. The United States Government has certain rights in this invention.

REFERENCE TO SEQUENCE LISTING

Applicants incorporate by reference the enclosed diskette containing Sequence Listing. A printout of the Sequence Listing follows the abstract.

BACKGROUND (1) Technical Field

The present invention relates to a method of treatment in dentistry and orthopedic surgery. More specifically the method provides for improving the seating of an implant in bone and for regenerating a periodontal ligament in the treatment of periodontal disease by administering a combination of cementum attachment protein and cyclosporin A.

(2) Background Art

The roots of teeth are attached to alveolar bone by dense, coronally oriented collagen fibers termed the periodontal ligament (FIG. 1). This ligament is embedded in bone on the one side and anchored to the surface of the tooth root by a specialized connective tissue termed cementum. The periodontal ligament serves two important functions. First it binds teeth to bone in a firm, but not rigid, manner. When forces are applied, suspension of the tooth in the periodontal ligament permits slight movement of the tooth in all directions. Through this mechanism large occlusal forces are transmitted to bone and resolved. Second, the periodontal ligament functions as a barrier restricting access of bacteria to the roots of teeth.

In the absence of such restriction bacteria can penetrate to the connective tissues surrounding the roots of teeth and elicit a destructive inflammatory response. The infection spreads apically between the teeth and gums and destroys the periodontal ligament, cementum and alveolar bone. The first objective in treating periodontal disease is to remove the microbial deposits from the roots of teeth by scaling and root planing. The second objective is to regenerate a fuinctional attachment of teeth to alveolar bone. A key component of such attachment is the periodontal ligament. Despite much effort it has not so far been possible to regenerate a periodontal ligament (Caffesse R G, de la Rosa M, and Mota IF "Regeneration of soft and hard tissue periodontal defects" Am J Dent 15: 339–245, 2002; Needleman I, Tucker R, Gledrys-Leeper E, Worthington H "A systematic review of guided tissue regeneration for periodontal infrabony defects"J Periodont Res 37: 380–388, 2002). Regenerating a periodontal ligament remains as a major objective for treatment of periodontal disease.

Periodontal disease can lead to tooth loss, and the preferred way to replace teeth is by dental implants. Titanium dental implants are having a major impact on dental practice. Technologically, the most remarkable feature is the development of a biologic union (osscointegration) of the titanium implant surface with bone. However, the problem with this union is its complete rigidity, which increases the likelihood of fractures, loosening of attachment screws and other complications. The rigidity of implants also prevents their use in fixed bridges, splints and other prostheses that include natural teeth as abutments. Such problems would be less likely to occur if there were a non-rigid connective tissue sling, like the periodontal ligament naturally occurring around teeth, between the implants and bone surfaces. Inducing the formation of a periodontal ligament around dental implants would improve their function and survival. The presence of cementum is thought to be required for the formation of a periodontal ligament.

To regenerate cementum or any other specialized tissue, it is necessary to attract cells able to produce the constituents of that tissue, secure the attachment of the cells to the intercellular substratum in the desired site, and induce their differentiation into cells secreting tissue-specific constituents. Cell. type-specific chemotactic factors, attachment factors, growth factors and differentiation factors mediate these functions.

Until recently the identity of these factors in cementum was unknown. During the past decade it has been established that the organic matrix of cementum contains attachment proteins not detectable in adjacent structures and a growth factor. Proteins active towards cementum-forming cells (cementoblasts) have been purified and many of their properties defined. A subset of connective tissue cells able to produce cementum has also been characterized. These alkaline-phosphatase-positive cells have properties suggesting that they are connective tissue precursor cells which have commenced differentiation towards the lineage of cementoblasts. Cementoblasts are found alongside blood vessels in the periodontal ligament.

Cementum attachment protein (CAP) is a 57 kilodalton (kDa) collagenous protein which is different from other collagen types and adhesion molecules. The expression of CAP is confined to mineralized tissue-forming cells and precursors originating in the periodontium, so that CAP can be used to identify cells of ccmentoblastic lineage (Liu, HW, Yacobi R, Savion, N, Narayanan AS and Pitaru S. "A New Collagenous Cementum-Derived Attachment Protein is a Marker for Progenitors of the Mineralized Tissues Forming Cell Lineage of the Periodontal Ligament." J Bone Mineral Res 12:1691–99, 1997). Peridontal cells migrate in response to and attach better to CAP-coated surfaces than do gingival fibroblasts (Pitaru, S. et al. "Specific cementum attachment protein enhances selectively the attachment and migration of periodontal cells to root surfaces." J. Periodont Res 30:360–68, 1995). We therefore proposed in a previous filing the use of CAP to induce the formation of cementum and a periodontal ligament around dental and orthopedic implants. We have now demonstrated that CAP does, in fact, have this effect, but only under certain conditions.

Turning to another related problem, means of stabilizing of implants used in orthopedic procedures, such as operations to restore joint motion known as arthroplasties, are still being sought. An example is total hip replacement consisting of a stemmed metal replacement for the femoral head articulating with a high-density polyethylene acetabular component, both components fixed to bone by polymethylmethacrylate (PMMA) cement. Similar procedures are used in the knee and other joints. PMMA cement is an insoluble material to fix the components securely in bone and to transfer stresses from the surface of the components to the larger bone surface, thereby reducing the acceptable pressure per unit of the surface. The cement is regarded as the weakest link in the bone-cement-implant composite (Tooms RE, and Harkness JW. "Arthr Introduction and Overview." In Campbell's Operative Orthopedics, 8$^{th}$ ed, Crenshaw AH, editor, Mosby Year Book, St. Louis, 1992, pp 371–87).

PMMA is technically difficult to use. PMMA is applied as a thick solution. If the polymer is too viscous, it does not easily enter into all the spaces between the implant and bone; if it is too liquid, the strength after polymerization may be inadequate. Even though PMMA is. a cold-curing polymer, the polymerization reaction is exothennic and can generate enough heat to damage tissues locally, as confirmed by histological studies. PMMA is a rigid, brittle solid, which can withstand high compression but fails under tension or shear forces. If there is any movement between the bone and implant surfaces, or if bone is resorbed for any reason, the cement can break. Fragments of PMMA, with a surrounding giant cell response, are often observed. Fragmentation of cement can limit the long-term survival and functional utility of implants, particularly in young and active persons. Allergic reactions to PMA have also been related to limited survival of implants. For these reasons the metal prosthesis is sometimes inserted into bone without PMMA, but such insertions do not always give satisfactory results, and a better procedure is needed.

Another difficult procedure in orthopedics is the attachment or re-attachment of tendons or ligaments to bone. Such a procedure is used in of traumatic ruptures, tendinitis, tendon transfers and other situations. Even before trauma, the direct insertion of a ligament or tendon into bone is a complex structure. At the insertion, collagen fibrils pass directly from the tendon, ligament or joint capsule into the bone cortex. The fibrils may pass through transitional zones of fibrocartilage and mineralized fibrocartilage. Such direct insertions are difficult to repair: a successful surgical procedure may not be accompanied by a return to normal function.

In an attempt to improve healing, collagen implants with additives such as various collagens, fibronectin, platelet derived growth factor (PDGF), bone morphogenetic proteins (BMPs), growth factors, vitamin D or hormones have been proposed in U.S. Pat. No. 5,002,583 to Pitaru, Gan and Noff. A special procedure bonds plastic to the implant. The outer collagen layer is intended to stimulate collagen ingrowth and anchoring. It was believed that these materials would be sufficient to create a biological bond between the surface of the implant and surrounding tissues.

A method for periodontal regeneration was disclosed by Antoniades and Lynch in U.S. Pat. No. 5,124,316. Basically, a growth-promoting amount of a growth factor, such as PDGF, was taught. According to the disclosure, factors inducing differentiation of precursors into cells with cartilage-forming or bone-forming capacity can also be administered. No factors specific formation are disclosed, nor is a method of reattaching ligaments or tendons to bone.

A composition containing an extract of enamel matrix from tooth germs for inducing bonding between mineralized tissue parts was disclosed by Hammarstrom, Blomlof and Lindskog in U.S. Patent No. 5,418,221. The active components in the extract have been defined, but its periodontal regeneration properties are reported to be in the fraction containing the enamel matrix proteins amelogenins, which are different from CAP and CGF (Hammarstrom L, Heijl L, and Gestrelius S. "Periodontal Regeneration in a Buccal Dehiscence Model in Monkeys After Application of Enamel Matrix Proteins." J Clin Periodontol 24:669–77, 1997). These investigators did not find cell-adhesion activity or growth factor in their preparations (Gestrelius S. Andersson C, Linstrom D, Hammarstrom L and Somerman M. "In vitro Studies on Periodontal Ligament Cells and Enamel Matrix Derivative." J Clin Pcriodontol 24:685–92, 1997).

A problem with the first two methods is that they are not specific enough to prevent osseointegration and to induce formation of the specialized structures (cementum and a periodontal ligament) required for providing a natural anchor for a dental or orthopedic implant. The dense coronally oriented collagen fibers of the truc periodontal ligament not only anchor implants to bone in a firm, but not rigid, manner, they also limit penetration of bacteria into connective tissues around the implant. Following implantation, loose connective tissues around the implant quite often become infected, resulting in inflammation and marginal bone resorption. A correctly reconstituted periodontal ligament could decrease the risk of this complication.

As for Hammarstrom's enamel extract, when we prepared it, we detected no CAP by biochemical procedures. Moreover, it would be preferable to use a defined, purified protein.

It was published that cyclosporin A (CSA) augments the formation of cementum in the rat (Ayanoglou CM, Lesty C. New cementum formation induced by cyclosporin A: a histological, ultrastructural and histomorphometric study in the rat. J Periodont Res 32: 543–556, 1997). These studies were performed in rats with intact teeth. There is no information on effects of CSA on dental or orthopedic implants, or on synergistic effects with CAP.

SUMMARY OF THE INVENTION

The present invention describes a combination of purified or recombinant cementum attachment protein (CAP) and a calcineurin inhibitor such as cyclosporin A (CSA) which induces the formation of cementum and of a functional periodontal ligament between an implant and bone.

In another embodiment, there is a pharmaceutical composition comprising an excipient, CAP and a calcineurin inhibitor such as CSA. The CAP can be an active fragment of the molecule. The active fragment may be at least a portion of SEQ ID NO 2.

In another embodiment the combination of CAP and CSA is administered with PDGF, insulin-like growth factor I (IGF-I), IGF-II, transforming growth factor $\beta$-1 (TGF-$\beta$1), TGF-$\beta$2, TGF-$\alpha$, bone morphogenic protein (BMP), osteogenin or a combination thereof.

In another embodiment, there is a method of providing normal seating of an implant. The method has the steps of preparing an operative site by removing the tissue to be replaced; administering into the operative site effective amounts of CAP and a calcineurin inhibitor; placing the implant; and closing the operative site. Preferably the calcineurin inhibitor is CSA.

In yet another embodiment, the effective amounts of CAP and CSA are those sufficient to induce cementoblast migration and synthetic activity resulting in ligamentous attachment of implant to bone.

In another embodiment, the step of administering CAP and CSA into the operative site is replaced by coating an implant with a pharmaceutical formulation comprising CAP and a calcineurin inhibitor such as CSA.

Also provided is a kit comprising an implant and a pharmaceutical formulation of CAP and CSA.

In another embodiment, CAP and CSA can be provided in a slow-release formulation, as a coating of an implant or as a separate pharmaceutical formulation.

In another embodiment, a method of improving regenerative therapy for periodontal disease includes the steps of cleaning at least one root of at least one tooth by planning and applying CAP and a calcineurin inhibitor to at least one root, thereby inducing the deposition of cementum and a periodontal ligament, which facilitates recovery from periodontal disease.

In another embodiment CAP and CSA are used to induce the formation of cementum and a dense, vertically oriented collagenous attachment of orthopedic prostheses to bone.

In yet another embodiment an improved method for reattaching a fibrous structure to a bone has the steps of preparing an operative site by isolating the fibrous structure and the bone to which it is to be attached; placing effective amounts of CAP and a calcineurin inhibitor where fibrous tissue is applied to bone; and ligating the fibrous structure to the bone, whereby the attachment of the fibrous structure to bone is strengthened. Thus, CAP and CSA are used to strengthen the attachment of tendons, ligaments and joint capsules to bone.

BRIEF DESCRIPTION OF THE DRAWINGS

FIG. 1 is a slide showing a cross section of a normal tooth and its periodontal ligament.

FIG. 2 depicts the implants placed into the dogs' jaws. The dotted line indicates the relationship of the bony surroundings to the implant.

FIGS. 3A–3D are cross sectional views of the implants in situ. FIGS. 3 A and 3B are from a dog receiving CAP and CSA. FIG. 3C shows an implant with collagenous tissue. FIG. 3D shows an implant onto which bone has grown.

DETAILED DESCRIPTION

As now reported, we have surprisingly found that when CAP and CSA are used together as a coating for titanium implants in dogs, they induce the formation of a dense coronal fibrous attachment with the properties of a periodontal ligament. That was the objective of the procedure. Neither CAP alone nor CSA alone had this desirable effect. These findings could not have been predicted from published information and are therefore novel. Hence the claim is made for a kit containing CAP and CSA, which can coat dental implants or be inserted into the implantation site, improving attachment and prolonging the life of the implants. A kit of similar composition, placed on the roots of teeth previously cleaned by root planing, will induce the formation of cementum and a periodontal ligament, thereby facilitating regenerative treatment for periodontal disease. A formulation of CAP and CSA will also improve the attachment of orthopedic prostheses to bones, as well as the attachment of ligaments, tendons and joint capsules to bone.

CAP and CSA, released into the space between titanium dental implants and bone, attracted cementoblasts, allowed them to attach and spread alongside the implants. CAP and CSA induced the cementoblasts to secrete constituents of cementum. Coronally oriented collagen fibers then attached the newly formed cementum to bone. In this manner cementum and a connective tissue attachment like a periodontal ligament are reproduced. A titanium dental implant attached to bone through a non-rigid periodontal ligament is less susceptible to fractures and other complications than is a titanium implant rigidly integrated into bone. Furthermore, such implants are suitable for inclusion with natural teeth in fixed bridges, splints and other prostheses. Another advantage of connective tissues around implants thus anchored to bone is better protection against infection at the bases of implants than in the absence of a periodontal ligament.

For treatment of periodontal disease CAP and CSA are applied to the surfaces of tooth roots previously cleaned by root planing. This combination, in a suitable formulation, induces the deposition of cementum on the tooth root and a periodontal ligament. The latter strengthens the attachment of teeth to alveolar bone and retards the penetration of bacteria to the tooth roots, thereby improving regenerative treatment.

For orthopedic implants, replacement of PMMA with natural cementum can be accomplished with the inventive method. CAP and/or CSA, slowly released between the implant and bone surfaces, induce the deposition of cementum firmly attached to the implant. Dense, perpendicularly oriented collagen fibers then bridge the space between cementum and bone in a firm but non-rigid manner, transferring stresses from the implant to a large bone surface in such a way as to reduce the pressure per unit surface. Cementum with this type of attachment to bone is less likely to fracture than is PMMA cement. The CAP and/or CSA procedure is easier to use in practice than is PMMA, and the former will produce less tissue damage. Implants attached to bone through cementum and collagen fibers vertically integrated into bone are expected to survive and function longer, and with fewer failures, than implants cemented with PMMA or inserted without any adhesive. Implants are typically made of titanium but can be made of any nonreactive material.

In tendon, ligament or capsule repair, the use of CAP and CSA at the site of insertion to bone induces the formation of a dense network of collagen fibers and their penetration perpendicularly through cementum into the bone cortex and thus bind the tendon, ligament or joint capsule to bone. This provides a functionally effective union of tendon to bone. The induced cementum functions in a manner analogous to the mineralized fibrocartilage naturally occurring in direct insertions.

Definitions:

Cementum attachment protein (CAP) is a protein of molecular mass approximately 56 kDa present in cementum and specifically expressed by mineralized tissue-forming cells of the periodontium. CAP promotes the attachment and spread of cells from the periodontal ligament more efficiently than that of gingival fibroblasts. The protein has sequences containing Gly-X-Y repeats typical of a collagen helix. SEQ ID NOS 1–5 are fragments of CAP. One 17-amino-acid peptide, SEQ ID NO 2, has 82% homology with a type XII collagen domain. However, type XII collagen does not promote the attachment of periodontal ligament cells. Although another 19-amino-acid-long peptide (SEQ ID NO 3) has 95% homology to bovine al (I) collagen, two other peptides, SEQ ID NOS 4 and 5, are only 79% and 68% homologous. CAP does not react with polyclonal antibodies against types I, V, XII, or XIV collagen or osteopontin, vitronectin or other attachment proteins. Bacterial collagenase was found to eliminate the capacity of CAP to promote attachment of periodontal cells; whereas, chondroitinase ABC digestion had no effect. These and other observations show that CAP is a collagenous attachment protein, localized in cementum, which is different from other known collagens and attachment proteins.

"Active portion thereof" is a portion of a protein which provides a desired activity. An active portion of CAP is a part of the molecule which is less than the whole but which still has a desired activity. The active portion may constitute any fraction of the molecule with that activity. A specific example includes but is not limited to SEQ ID NO 2.

"Purified" as used herein refers to CAP which, prior to mixing with a carrier substance, is 95% or greater by weight, e.g., the factor is substantially free of other proteins, lipids, carbohydrates with which it is naturally associated. The term "partially purified" refers to a lesser purity of factor, having, for example, only 50–95% by weight of the factor, preferably 65–90%. A purified protein preparation generally yields a single major band on a polyacrylamide gel. Most preferably, purified CAP used in compositions of the invention is pure as judged by amino-terminal amino acid sequence analysis.

Cyclosporin A was used in the experiments detailed below. Because cyclosporin A is a calcineurin inhibitor, it is expected that others calcineurin inhibitors would be useful in this invention. Another example of a calcineurin includes, but is not limited to tacrolimus (Prograf®, Fujisawa Healthcare, Inc., Deerfield, IL).

"Fibrous structure," as used herein, refers to tendons, ligaments and joint capsules which may need to be attached to bone.

EXAMPLES

The following examples are given to enable those skilled in the art to more clearly understand and to practice the invention. They should not be considered as a limitation of the invention, but merely as being illustrative and representative thereof.

Preparation of CAP

A highly purified bovine CAP preparation was disclosed in Wu et al., "Characterization of a Collagenous Cementum-Derived Attachment Protein." J Bone Miner Res 11:686–692, 1996. CAP can be produced by other less effective methods. Human CAP can be prepared similarly. Briefly, CAP was first extracted from cementurn in 2.0 N HCOOH containing proteinase inhibitors and then with 4M guanidine HCI. Guanidine extracts were loaded on a diethylarnino ethyl (DEAE) cellulose column for chromatography, and next purified by sodium dodecyl sulfate (SDS)-polyacrylamide gel electrophoresis and C18 reverse-phase high-performance liquid chromatography. The purified preparation contained a single protein band electrophoretically migrating with 56,000 Daltons in SDS-polyacrylamide gels.

Wu et al. also obtained the internal amino acid sequences of six peptides by microsequencing. First, the purified CAP was digested with endoproteinase Lys-C or TPCK-ttypsin at enzyme: substrate ratio of 1:25 at 37° C. for 6–12 hours. Subsequently the peptides were separated in a microbore column of Aquapore RP-300-C-8 (2.1×l100 mm, 7 mm, Pierce) and eluted with a linear gradient of 0–55% $CH_3CN$/O. 1% TFA. Fractions were collected and peptides were microsequenced in an Applied Biosystems 470A gas-phase sequencer equipped with an online model 120 Pth analyzer. The sequences of these peptides are shown as SEQ ID NOS 1–5. There were no perfect matches for the peptides in public computer databases as of Dec. 2, 1997.

The amino acid sequences of CAP did not match those of fibronectin, laminin, osteopontin, bone sialoprotein or vitronectin which are present in cementum and have been postulated as the source of CAP. The sequences also are distinct from those of amelogenins. SEQ ID NOS 2–5 contain Gly-X-Y repeats characteristic of the collagen triple helix. SEQ ID NO 2 had 82% homology with a 17-amino acid stretch of al Collagen XII; however, CAP did not cross-react with anti-Collagen XII (which was specific for a different domain). SEQ ID NOS 3–5 also do not have perfect matches with other collagens.

Recombinantly produced CAP

Using the unique portions of the amino acid sequences, collections of degenerate cDNA probes are synthesized and combined with suitable DNA tissue constructed from expressed mRNA. Alternately, the degenerate probes are used against genomic libraries. We have also obtained several monoclonal antibodies to CAP, which can be used to identify clones producing CAP genetically engineered into the clones. Either way, partial- or full-length DNA which codes for CAP can be obtained and replicated to sufficient quantity to sequence. Once the complete coding sequence has been obtained, the DNA encoding CAP can also be genetically engineered into a vector that is then used to transform cells to produce CAP. The DNA coding sequence can be optimized by a commercial computer program to replace human-preferred codons with the codons preferred by the cells chosen to replicate the protein.

The optimal organism or cell line is one with a high yield of protein, including proper folding and post-expression modification, as needed. Preferably the CAP DNA is expressed in conjunction with a fusion protein which helps purify CAP, without interfering with its proper folding. Alternately, CAP can be purified on a column with the CAP antibody.

In addition, the protein can be produced by chemical synthesis. This method is particularly useful for relatively short, active portions of the molecule.

Alternatively, only the active portion of CAP need be administered. For example, a peptide of CAP incorporating at least a portion of SEQ ID NO 2, which binds to cells, is administered without the rest of the molecule. In addition, an active portion of the molecule can be expressed with a homing device, such as an antibody with narrow specificity for the cell type or tissue which is to be activated. This mechanism can localize the induction activity only at the essential site and help avoid untoward effects.

The gene for human CAP is cloned and efficiently expressed in an appropriate system, and the recombinant proteins are used to induce the formation of cementum and a periodontal ligament. The protein naturally occurring in the organic matrix of cementum, CAP, exemplifies a factor able to attract cementoblasts to the operation site. CSA also induces the formation of cementum and a periodontal ligament. The two agents, used together, induce the formation of a periodontal ligament.

Formulation

Slow release of these proteins can be achieved by well-known procedures. Examples are release of proteins adsorbed onto the bases of the implants or released from hydroxyapatite, tricalcium phosphate or other materials, from biodegradable particles such as those composed of polylactide-co-glycolide, from inert gels or liquids (e.g., propylene glycol, alginate, carbopol, methylcellulose and derivatives), or from microstructures combining organic and inorganic materials.

Testing

Popular test models are implantation of titanium implants into the mandibles of dogs or monkeys. FIG. 1 shows a normal dog tooth root with periodontal ligament fibers. Previously, implants placed alongside retained apical roots have been found to generate a cementum layer on the implant surface, with perpendicularly inserted collagen fibers forming a periodontal ligament (Buser D, Warren K, Karring T, and Stich H. Titanium Implants with a True Periodontal Ligament: an Alternative to Osseointegrated Implants?Int J Oral Maxillofacial Implants 5:113–16, 1990). Their control implants did not contact retained roots and demonstrated the typical findings of osseointegration. The present invention achieves deposition of cementum and a periodontal ligament around dental implants in the absence of retained roots.

Mandibular premolar teeth were extracted bilaterally from young adult Beagle dogs, and the bony sockets allowed to heal completely. This allowed sufficient edentulous space to place six implants in each dog. Titanium implants were custom crafted such that the most coronal portion would fit snugly into the bony socket prepared to receive the implant, but a space of 0.5 to 1.0 mm would exist between the bone (- - -) and the implant surface in the apical three-fourths of the implant (FIG. 2). The titanium implants had a surface comparable to implants used in humans. Half of the implants were coated with hydroxyapatite (HA) by the manufacturer and the other half were uncoated titanium (Ti). Using both Ti and HA implants, CAP and CSA were used together and separately to evaluate their capacity to induce the formation of a peri-implant ligament. Coated and uncoated implants were placed in dogs. Four surface conditions were tested including HA and Ti; HA+CAP and Ti+CAP; HA+CSA and Ti+CSA; HA+CAP+CSA and Ti+CAP+CSA.

Following standard protocols, the implants were placed in edentulous mandibular bone in the dogs and the gum flaps sutured. After a healing period of three and one-half months, the animals were sacrificed and block sections of the jaws containing the implants were harvested. Following fixation, calcified specimens were embedded in plastic; histologic sections were prepared, treated with trichrome stains and examined in the light microscope.

Only the Ti surfaces coated with CAP+CSA manifested implants with oriented peri-implant ligament collagen fibers attached to the implant surface on one end and alveolar bone on the other (FIGS. 3A, 3B). Under all other conditions, the space between the implant surface and the bony socket was filled with collagen fibers with no specific orientation or with new bone that contacted the implant surface (FIGS. 3C, 3D). In this animal model, titanium implants coated with CAP and CSA, but not CAP alone nor CSA alone, were attached to alveolar bone by a well-oriented peri-implant collagen fiber structure similar to that observed around natural teeth.

These experimental findings demonstrate that it is possible to induce the formation of a periodontal ligament around titanium dental implants, but that this occurs only under particular conditions. These conditions could not have been predicted from known information about CAP and CSA, and are therefore unexpected. The novel combined CAP and CSA coating has the potential to improve significantly dental implants. A logical extension of these findings would be to use CAP and CSA as a coating for orthopedic implants, thereby producing a firm but slightly flexible attachment to bone, which is desirable. This is a completely novel concept since natural cementum is confined to teeth and is not present in the femur or other bones involved in arthroplasty and other orthopedic procedures.

What is claimed is:

1. A pharmaceutical composition comprising cementum attachment protein (CAP), cyclosporine A and an excipient.

2. composition of claim 1 further comprising PDGF, insulin-like growth factor I (IGF-I), IGF-II, transforming growth factor β-1 (TGF-β1), TGF-β2, TGF-α, bone morphogenic protein (BMP), osteogenin thereof.

3. The composition of claim 1 in which the composition is in a slow release formulation.

4. A method of improving attachment of a dental or orthopedic implant comprising:
   a) preparing an operative site by removing the tissue to be replaced;
   b) administering an effective amount of the pharmaceutical composition of claim 1 into the operative site; and
   c) placing the implant.

5. The method of claim 4, wherein an effective amount of the pharmaceutical composition is sufficient to induce cementoblast migration and synthetic activity.

6. The method of claim 4, wherein step b is replaced by the step of coating an implant with a pharmaceutical formulation comprising CAP and cyclosporine A.

7. A kit comprising an implant and the pharmaceutical composition of claim 1.

8. A method of improving regenerative therapy for periodontal disease comprising
   a) cleaning at least one root of at least one tooth by planing; and
   b) applying CAP and cyclosporine A to at least one root, thereby inducing the deposition of cementum and formation of a periodontal ligament which facilitates recovery from periodontal disease.

9. An improved method for reattaching a fibrous structure to a bone, the method comprising:
   a) preparing an operative site by isolating the fibrous structure and the bone to which it is to be attached;
   b) placing effective amounts of CAP and cyclosporine A where fibrous tissue is applied to bone; and
   c) ligating the fibrous structure to the bone, whereby the attachment of the fibrous structure to bone is strengthened.

10. The method of claim 9, wherein the fibrous structure is a ligament, tendon or joint capsule.

* * * * *

UNITED STATES PATENT AND TRADEMARK OFFICE
CERTIFICATE OF CORRECTION

PATENT NO. : 7,071,162 B1  
APPLICATION NO. : 10/410762  
DATED : July 4, 2006  
INVENTOR(S) : Narayanan et al.

Page 1 of 1

It is certified that error appears in the above-identified patent and that said Letters Patent is hereby corrected as shown below:

Column 2, line 8, "osscointegration" should read --osseointegration--.

Column 5, line 13, "planning" should read --planing--.

Column 7, line 23, "usefuil" should read --useful--; line 43, "cementurn" should read -- cementum--; line 46, "larnino" should read --lamino--; line 55, "ttypsin" should read --trypsin--; line 58, "1100" should read --100--.

Column 11, lines 43-46, cancel the text beginning with "2. composition" and ending with osteogenin thereof.", and insert the following claim:

2. A composition of claim 1 further comprising PDGF, insulin-like growth factor I (IGF-I), IFG-II, transforming growth factor beta-1 (TGF-beta1), TGF-beta2, TGF-alpha, bone morphogenic protein (BMP), osteogenin or a combination thereof.

Signed and Sealed this

Twenty-fourth Day of July, 2007

JON W. DUDAS  
*Director of the United States Patent and Trademark Office*

UNITED STATES PATENT AND TRADEMARK OFFICE
CERTIFICATE OF CORRECTION

PATENT NO. : 7,071,162 B2 Page 1 of 1
APPLICATION NO. : 10/410762
DATED : July 4, 2006
INVENTOR(S) : A. Sampath Narayanan et al.

It is certified that error appears in the above-identified patent and that said Letters Patent is hereby corrected as shown below:

On the title page, item [75] add 5$^{th}$ inventor to read
--Higinio Arzate, Xochimilco, Mexico--.

Signed and Sealed this

Twentieth Day of May, 2008

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 12
<212> TYPE: PRT
<213> ORGANISM: homo sapiens
<220> FEATURE:
<221> NAME/KEY: UNSURE
<222> LOCATION: (7)..(10)
<223> OTHER INFORMATION: amino acids 7 and 10 are unknown

<400> SEQUENCE: 1

Leu Pro Gln Met Phe Ala Xaa Gln Cys Xaa Lys Ile
 1               5                  10

<210> SEQ ID NO 2
<211> LENGTH: 17
<212> TYPE: PRT
<213> ORGANISM: homo sapiens
<220> FEATURE:
<221> NAME/KEY: UNSURE
<222> LOCATION: (15)
<223> OTHER INFORMATION: amino acid 15 is unknown

<400> SEQUENCE: 2

Lys Gly Phe Thr Gly Ala Asp Gly Pro Gln Gly Pro Arg Gly Xaa Pro
 1               5                  10                  15

Gly
```

-continued

```
<210> SEQ ID NO 3
<211> LENGTH: 19
<212> TYPE: PRT
<213> ORGANISM: homo sapiens

<400> SEQUENCE: 3

Lys Arg Gly Ala Arg Gly Glu Pro Gly Pro Ala Gly Leu Pro Gly Pro
 1               5                  10                  15

Pro Gly Glu

<210> SEQ ID NO 4
<211> LENGTH: 24
<212> TYPE: PRT
<213> ORGANISM: homo sapiens
<220> FEATURE:
<221> NAME/KEY: UNSURE
<222> LOCATION: (21)
<223> OTHER INFORMATION: amino acid 21 is unknown

<400> SEQUENCE: 4

Gly Ala Pro Gly Pro Pro Gly Pro Pro Gly Phe Ala Gly Pro Pro Gly
 1               5                  10                  15

Ala Asp Gly Ala Xaa Gly Ser Arg
            20

<210> SEQ ID NO 5
<211> LENGTH: 19
<212> TYPE: PRT
<213> ORGANISM: homo sapiens

<400> SEQUENCE: 5

Gly Leu Pro Gly Val Ala Gly Ser Val Gly Glu Pro Gly Pro Thr Gly
 1               5                  10                  15

Ile Ala Gly
```